United States Patent
Hsu et al.

(10) Patent No.: US 7,892,008 B2
(45) Date of Patent: Feb. 22, 2011

(54) ELECTRICAL CONNECTOR HAVING METALLIC LOCK

(75) Inventors: Shuo-Hsiu Hsu, Tu-Cheng (TW); Chi-Nan Liao, Tu-Cheng (TW)

(73) Assignee: Hon Hai Precision Ind. Co., Ltd., Taipei Hsien (TW)

( * ) Notice: Subject to any disclaimer, the term of this patent is extended or adjusted under 35 U.S.C. 154(b) by 0 days.

(21) Appl. No.: 12/569,914

(22) Filed: Sep. 30, 2009

(65) Prior Publication Data

US 2010/0081300 A1    Apr. 1, 2010

(30) Foreign Application Priority Data

Sep. 30, 2008    (TW) ............................... 97217524 U

(51) Int. Cl.
*H01R 13/62*    (2006.01)

(52) U.S. Cl. ....................................... 439/331; 439/893

(58) Field of Classification Search ................. 439/331, 439/892, 893
See application file for complete search history.

(56) References Cited

U.S. PATENT DOCUMENTS

| | | | | |
|---|---|---|---|---|
| 5,291,553 A * | 3/1994 | Smith | ..................... | 379/413.04 |
| 6,273,739 B1 * | 8/2001 | Konno et al. | ................. | 439/331 |
| 6,428,338 B1 * | 8/2002 | Yasufuku et al. | ............ | 439/310 |
| 6,971,919 B1 * | 12/2005 | Huang | ......................... | 439/630 |
| 7,544,097 B2 * | 6/2009 | Hong et al. | ................. | 439/626 |
| 2010/0055935 A1 * | 3/2010 | Hsu et al. | ...................... | 439/70 |
| 2010/0055939 A1 * | 3/2010 | Hsu | ............................. | 439/73 |
| 2010/0081300 A1 * | 4/2010 | Hsu et al. | .................. | 439/76.1 |
| 2010/0093196 A1 * | 4/2010 | Hsu et al. | ..................... | 439/80 |
| 2010/0105236 A1 * | 4/2010 | Mao | ........................... | 439/331 |
| 2010/0167592 A1 * | 7/2010 | Shimada | ..................... | 439/629 |

FOREIGN PATENT DOCUMENTS

TW    M244598    9/2004

* cited by examiner

*Primary Examiner*—James Harvey
(74) *Attorney, Agent, or Firm*—Andrew C. Cheng; Wei Te Chung; Ming Chieh Chang

(57) ABSTRACT

An electrical connector, for electrically connecting a module to a circuit substrate, comprises an insulative housing for loading a module, a plurality of contacts received in the insulative housing, a cover pivotally connecting to an end of the insulative housing and a pair of metal ears mounted to two sides of another opposed end of the insulative housing. The metal ear has an engaging portion, a spring arm upwardly extending from a top end of the engaging portion to lock the cover and a mounting portion downwardly extending from a bottom end of the engaging portion for soldering to the circuit substrate. The electrical connector can be easily operated and provide a reliable connection.

14 Claims, 4 Drawing Sheets though the apertures 33 will lift upwardly and then ride over a top edge of the apertures 33 automatically and reach and engage with a bottom edge of the apertures 33 to lock the cover 3 in the closed position.

ELECTRICAL CONNECTOR HAVING METALLIC LOCK

BACKGROUND OF THE INVENTION

1. Field of the Invention

The present invention relates to an electrical connector, and more particularly, to an electrical connector having two metal ears thereof interlocking a metallic cover closed to a housing.

2. Description of the Prior Art

TaiWanese Utility Patent NO. M244598 issued to Lu on Sept. 21, 2004 discloses a conventional electrical connector for electrically connecting a module with a PCB. The electrical connector comprises a socket body having a number of terminals received therein and a metallic cover pivotally assembled to the socket body. The socket body comprises a bottom wall and two sidewalls extending upwardly from the bottom wall. The bottom wall and the sidewalls jointly form a space for receiving the module therein. The cover has a base and two edges with a slot, and the side wall has a pinshaft received in the slot to pivotally assemble the cover to the socket body. The edge further has a latching finger bent inwardly therefrom to latch with a groove defined on a side wall of the socket body.

However, when the electrical connector is imposed by an external force and vibrations, the latching finger may easily disengage from the groove leaving the module disposed therein in jeopardized and can not be reliably attached to the socket body, that may cause loose of the cover.

In view of the above, an improved electrical connector is needed to overcome the above-mentioned disadvantages.

SUMMARY OF THE INVENTION

Accordingly, an object of the present invention is to provide an electrical connector having a pair of metal ears, which can keep the cover in a closed position.

To fulfill the above-mentioned object, an electrical connector for electrically connecting a module to a circuit substrate, comprises: an insulative housing, a plurality of contacts, a cover and a pair of metal ears. The insulative housing is used for loading a module therein, the contacts are received in the insulative housing, the cover pivotally connects to a rear end of the insulative housing. The metal ears is mounted to two sides of a front end of the insulative housing, the metal ear has an engaging portion, a spring arm upwardly extending from a top end of the engaging portion to lock the cover and a mounting portion downwardly extending from a bottom end of the engaging portion for soldering to the circuit substrate.

Other objects, advantages and novel features of the invention will become more apparent from the following detailed description when taken in conjunction with the accompanying drawings.

DETAILED DESCRIPTION OF THE PREFERRED EMBODIMENT OF THE INVENTION

Figure 1:
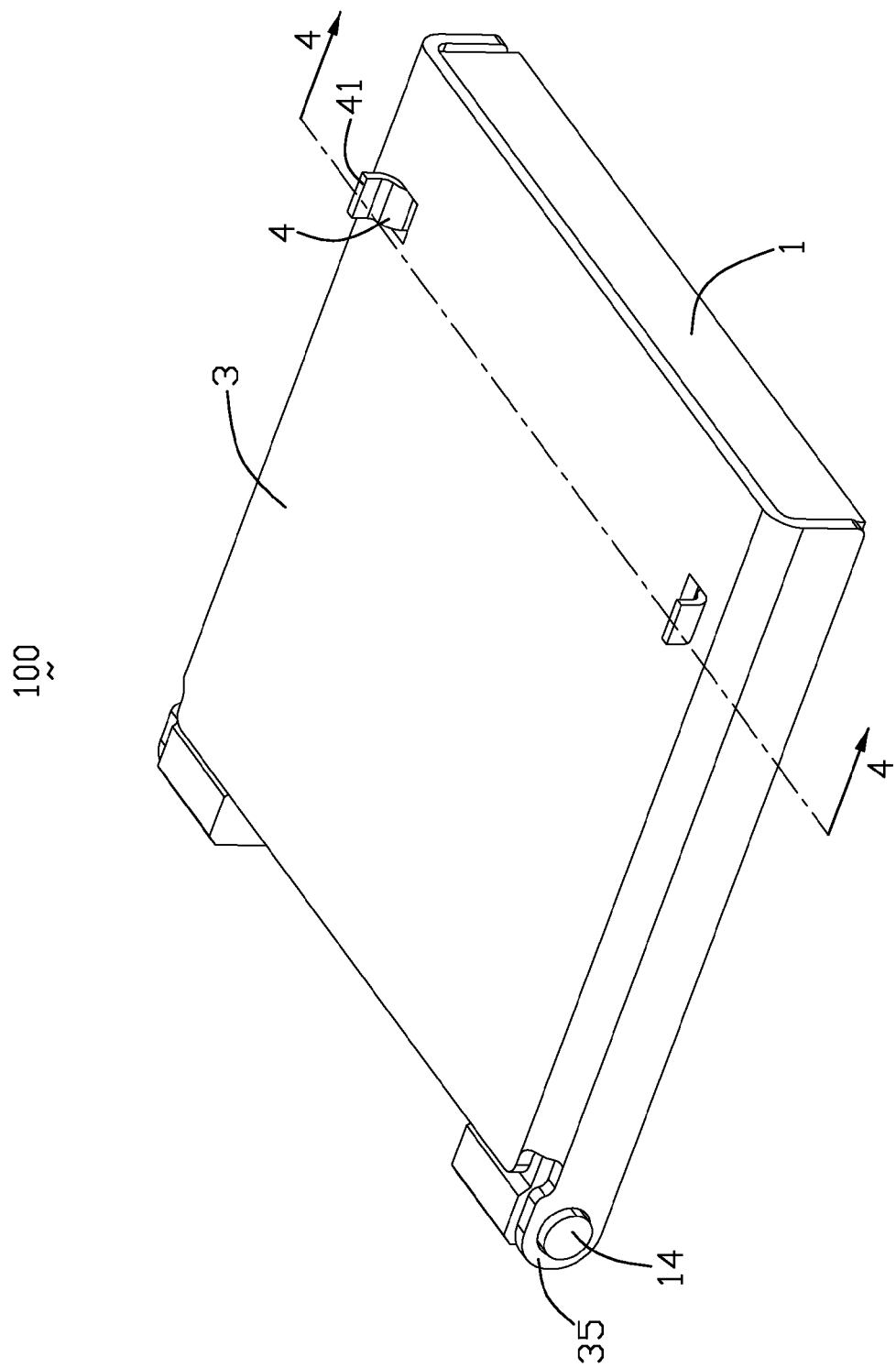
FIG. 1 is an assembled, perspective view of the electrical connector in accordance with a preferred embodiment of the present invention.
Figure 2:
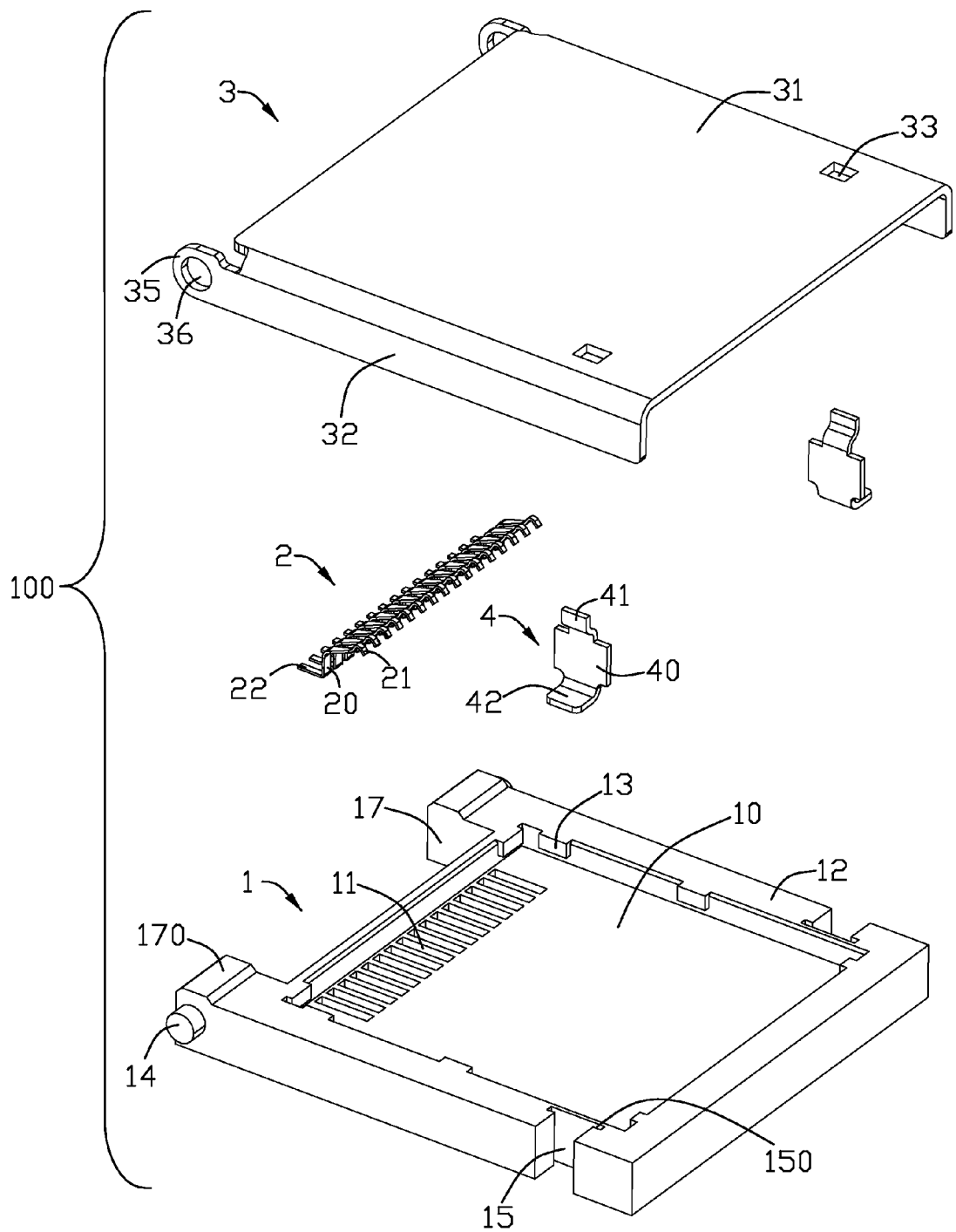
FIG. 2 is an exploded, perspective view of the electrical connector shown in FIG. 1.

Reference will now be made to the drawings to describe the present invention in detail.

Referring to FIGS. 1-4, an electrical connector 100 made in accordance with the present invention is used to convert optical signal from a module (not shown) into electrical signal and then transmitted to a circuit substrate (not shown), and vise versa. The electrical connector 100 comprises an insulative housing 1, a plurality of contacts 2 received in the insulative housing 1, a cover 3 pivotally assembled on the insulative housing 1 and two metal ears 4 received in the insulative housing 1 locking the cover 3 when the cover 3 is closed to the housing 1.

The insulative housing 1 is configured to a rectangular shape and comprises a base 10 and four sidewalls 12 extending upwardly from the base 10. The base 10 and the four sidewalls 12 jointly form a receiving space. The base 10 defines a row of passageways 11. The contact 2 comprises a main base 20, a contacting portion 21 extending upwardly from the main base 20, and a soldering portion 22 extending downwardly from the main portion 20. Those four sidewalls 12 each has a pair of datum blocks 13. The datum blocks 13 precisely position the module (not shown) therebetween such that electrical interconnection between the contacts and the module is ensured. A pair of the sidewalls 12 each has a protruding portion 17 at a rear end thereof, the protruding portion 17 has a protruding top face 170 and a column-shaped pinshaft 14 on an outside surface thereof. The pair of sidewalls 12 each defines a recess 15 at a front end thereof, the recess 15 defines a slot 150 on an inner side thereof for receiving the metal ears 4 therein. A plurality of posts 16 extend downwardly from a bottom surface of the base 10 of the insulative housing 1.

The metal ear 4 comprises a vertical engaging portion 40, a spring arm 41 extending upwardly from the engaging portion 40, and a mounting portion 42 extending curvedly and curvilinearly from the engaging portion 40. The engaging portion 40 is securely retained in the slot 150 of the recess 15, the spring arm 41 extends beyond the socket body 10 for engaging with the cover 3, and the mounting portion 42 is used for soldering to the circuit substrate (not shown).

The cover 3 is made of sheet metal and comprises a flat body plate 31 and two flanges 32 extending downwardly from the body plate 31. The body plate 31 has two apertures 33 on two sides thereof, and the apertures 33 has a rectangular shape for engagement with the spring arm 41 of the metal ear 4 as it passes through. The flange 32 has a pivoting portion 35 with a hole 36 at a rear end thereof.

Figure 3:
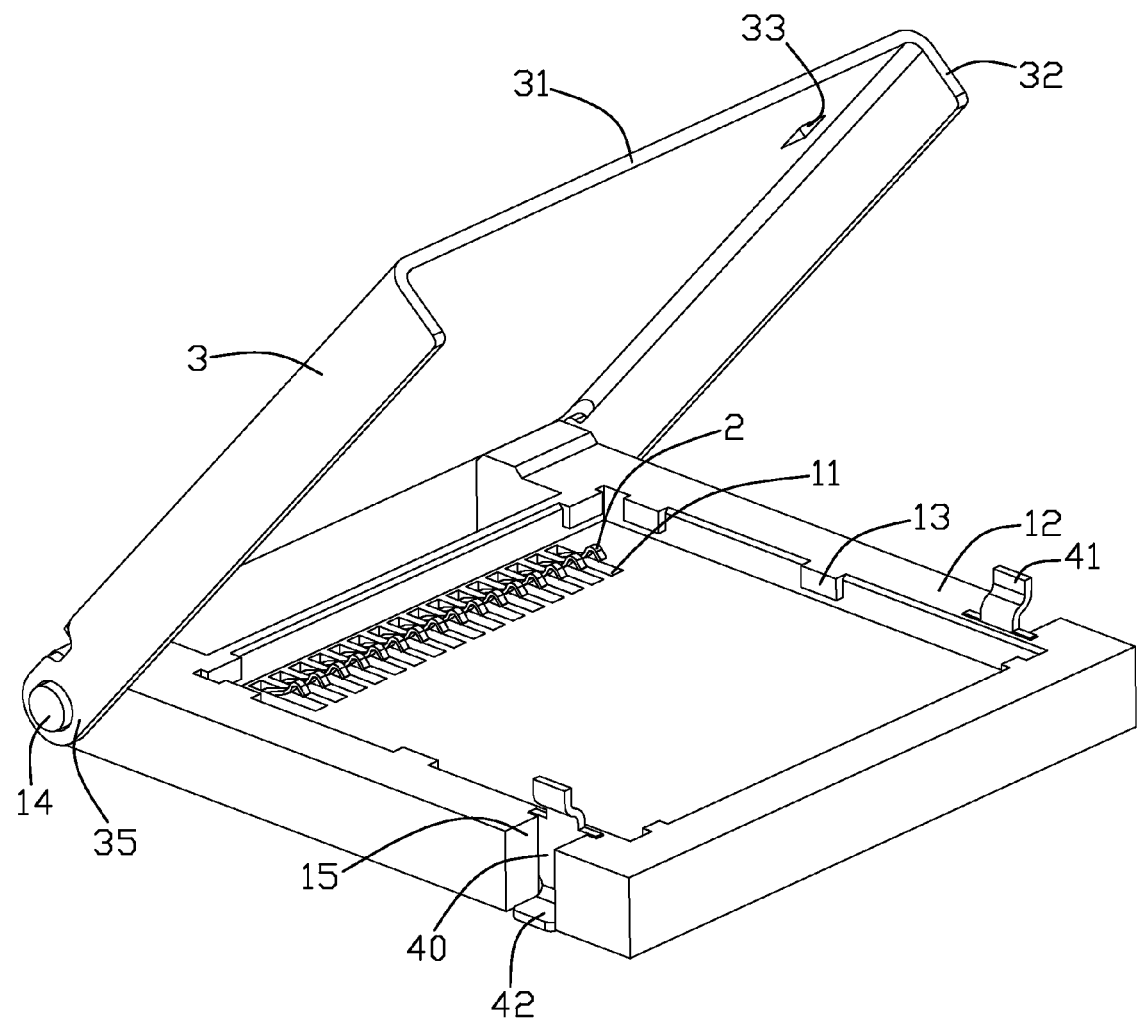
FIG. 3 is another assembled view of the electrical connector, showing the cover is in an opened position.

Referring to FIG. 3, the contact 2 are firstly received in the passageways 11 of the insulative housing 1, the metal ear 4 are securely set in the recesses 15, then the holes 36 of the pivoting portion 35 of the cover 3 surrounds the pinshafts 14 of the insulative housing 1, the pinshaft 14 protruding out of an outside surface of the aperture 36. The cover 3 can be located at an opened position and a closed position relative to the insulative housing 1.

Figure 4:
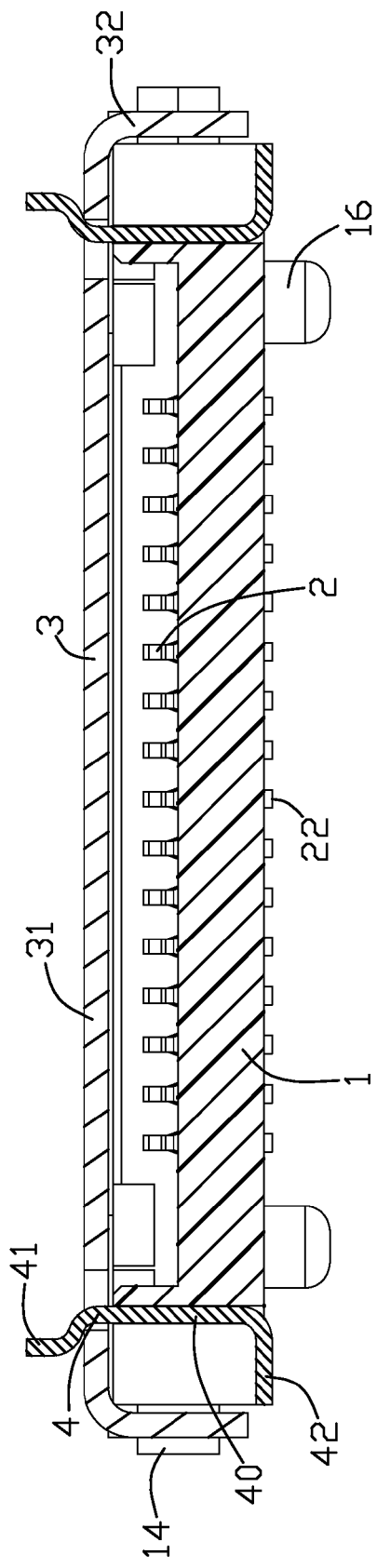
FIG. 4 is a cross-sectional view taken along line 4-4 of FIG. 1 in which the cover is latched.

Referring to FIGS. 1 and 4, when the cover 3 needs to be disengaged and move from the closed position to the opened position, firstly, the spring arms 41 protruding out of the apertures 33 of the cover 3 are pressed toward each other to release the locking thereof to the cover 3, and then the cover 3 can be readily lifted upwardly and then rotates to the opened position, the module (not shown) can be put in the base 10 and positioned precisely by the datum blocks 13. When the cover 3 moves to the closed position, the spring arm 41 passes through the aperture 33 of the cover 3 and locks with and edge of the aperture 33 to keep the cover 3 in the closed position, at this state, the contacts 2 are electrically contact with the module (not shown).

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed. For example, the cover 3 could be equipped with a torsion spring around the pin shaft 14 so as to automatically raise up the cover 3 once releasing the cover 3 from the metal ear 4.

What is claimed is:

1. An electrical connector, for electrically connecting a module to a circuit substrate, comprising:
    an insulative housing for loading a module therein;
    a plurality of contacts received in the insulative housing;
    a cover pivotally connecting to a rear end of the insulative housing; and
    a pair of metal ears mounted to two sides of a front end of the insulative housing, the metal ear having an engaging portion, a spring arm upwardly extending from a top end of the engaging portion to lock the cover and a mounting portion downwardly extending from a bottom end of the engaging portion for soldering to the circuit substrate.

2. The electrical connector as claimed in claim 1, wherein the insulative housing comprises a base and four sidewalls extending upwardly from the base, two opposed ones of the sidewalls each defines a recess at an end thereof, the recess defines a slot to receive the metal ear.

3. The electrical connector as claimed in claim 2, wherein the cover is made of sheet metal and comprises a flat body plate and two flanges extending downwardly from the body plate, the body plate has two apertures on two sides thereof, the spring arm of the metal ear passes through the aperture and locks with the aperture.

4. The electrical connector as claimed in claim 2, wherein the engaging portion is received in the slot of the recess.

5. The electrical connector as claimed in claim 1, wherein the base of the insulative housing has a plurality of posts extending downwardly thereof.

6. The electrical connector as claimed in claim 2, wherein the two opposed sidewalls each has a protruding portion with a column-shaped pinshaft disposed on an outside surface thereof.

7. The electrical connector as claimed in claim 6, wherein the flange of the cover has a pivoting portion with a hole, the pinshaft of the insulative housing inserts into the hole of the cover to assemble the cover on the insulative housing.

8. The electrical connector as claimed in claim 7, wherein the sidewalls each has a pair of datum blocks, the datum blocks together receive the module therebetween.

9. The electrical connector as claimed in claim 8, wherein the contact comprises a main base, a contacting portion extending upwardly from the main base, and a soldering portion extending downwardly from the main portion.

10. An electrical socket connector, for electrically connecting a module to a circuit substrate, comprising:
    an insulative housing including a platform with an array of passageway defined therein, and defining a first end and a second end;
    a plurality of contacts received in the passageway;
    a cover pivotally connecting to a first end of the insulative housing to substantially cover the insulative housing, the cover having two apertures; and
    a pair of metallic ears disposed on the housing to releaseably engage with the apertures when the cover is closed to the insulative housing; wherein each ear includes a releasing arm manipulated to disengage the cover from the ear.

11. An electrical connector comprising:
    an insulative housing defining an upper face with thereabove a module receiving space defining opposite ends thereof;
    a plurality of contacts disposed in the housing with contacting sections upwardly extending above the upper face;
    a cover pivotally assembled around one end of the module receiving space;
    a locking ear located around the other end of the module receiving space and locking a free end section of said cover; said locking ear is soldered to a printed circuit board to which said contacts are mechanically and electrically connected.

12. The electrical connector as claimed in claim 11, wherein said module receiving space is formed by the housing, and said locking ear is fastened to the housing.

13. The electrical connector as claimed in claim 11, wherein said cover is equipped with a torsion spring so as to automatically raise up the cover once the locking ear is released.

14. The electrical connector as claimed in claim 11, wherein said cover defines an opening through which said locking ear extends for locking.

* * * * *